US009739134B2

(12) United States Patent
Li et al.

(10) Patent No.: US 9,739,134 B2
(45) Date of Patent: Aug. 22, 2017

(54) CHARACTERIZATION METHOD FOR A RESERVOIR MICRO PORE STRUCTURE AND A SYSTEM THEREOF

(71) Applicant: PetroChina Company Limited, Beijing (CN)

(72) Inventors: Jianming Li, Beijing (CN); Xu Jin, Beijing (CN); Xiaoqi Wang, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 223 days.

(21) Appl. No.: 14/749,502

(22) Filed: Jun. 24, 2015

(65) Prior Publication Data

US 2015/0371818 A1 Dec. 24, 2015

(30) Foreign Application Priority Data

Jun. 24, 2014 (CN) .......................... 2014 1 0287262

(51) Int. Cl.
*E21B 47/00* (2012.01)
*G01N 15/05* (2006.01)
(Continued)

(52) U.S. Cl.
CPC .............. *E21B 47/00* (2013.01); *E21B 49/00* (2013.01); *G01N 15/088* (2013.01); *G01V 9/00* (2013.01)

(58) Field of Classification Search
CPC ....... E21B 47/00; E21B 49/00; G01N 15/088; G01N 33/24; G01V 9/00; C25D 5/54; C25D 5/56
See application file for complete search history.

(56) References Cited

U.S. PATENT DOCUMENTS 6,051,117 A * 4/2000 Novak ...................... C25B 9/00 204/252
6,365,415 B1 * 4/2002 Li .......................... B82Y 15/00 204/456

(Continued)

FOREIGN PATENT DOCUMENTS

CN 101216430 A 7/2008
CN 102183450 A 9/2011

(Continued)

OTHER PUBLICATIONS

Chen et al, "Overview of study method of resevoir rock pore structure", Special Oil and Gas Reservoirs; Aug. 2005; vol. 12, No. 4; 5 pages.
Geet et al, "Quantitative analysis of reservoir rocks by microfocus X-ray computerised tomography", Sedimentary Geology 132, 2000; 12 pages.
Hu et al, "Analysis of micro pore structure in low permeability reservoirs", China Academic Journal Electronic Publishing House; Jun. 2006; vol. 30, No. 3; 5 pages.

(Continued)

*Primary Examiner* — Louis Rufo
(74) *Attorney, Agent, or Firm* — LOZA & LOZA, LLP; Michael F. Fedrick

(57) ABSTRACT

The present application provides a method for characterizing reservoir micro pore structures, in particular structures smaller than 50 nm and a system therefore. The method can include fabricating a reservoir sheet; fabricating a reservoir sheet electrode using the reservoir sheet; depositing crystal substance in inner pores of the reservoir sheet of the reservoir sheet electrode using chemical deposition; obtaining the crystal substance by removing rock portions of the reservoir sheet in which the crystal substance is deposited; and scanning the shapes of the obtained crystal substance, the result of the scanning being the reservoir micro pore structure.

10 Claims, 6 Drawing Sheets fabricating a reservoir sheet
S1
fabricating a reservoir sheet electrode using the reservoir sheet
S2
depositing a crystal substance into pores of the reservoir sheet of the reservoir sheet electrode by using electrochemical deposition
S3
obtaining the crystal substance by removing a rock portion of the reservoir sheet in which the crystal substance is deposited
S4
scanning a morphology of the obtained crystal substance
S5

(51) Int. Cl.

| | |
|---|---|
| ***G01V 9/00*** | (2006.01) |
| ***E21B 49/00*** | (2006.01) |
| ***G01N 15/08*** | (2006.01) |

(56) References Cited

U.S. PATENT DOCUMENTS

| | | | |
|---|---|---|---|
| 6,714,871 | B1 | 3/2004 | Xu et al. |
| 2005/0206890 | A1 | 9/2005 | Hurst et al. |
| 2015/0371818 | A1 | 12/2015 | Li et al. |

FOREIGN PATENT DOCUMENTS

| | | | |
|---|---|---|---|
| CN | 103196807 | A | 7/2013 |
| CN | 103217370 | A | 7/2013 |
| CN | 103760081 | A | 4/2014 |
| CN | 104089863 | A | 10/2014 |

OTHER PUBLICATIONS

Liu et al, “A Feasible Method for Fractal Study Using Gas Adsorption Isotherm and Its Application in Earth Sciences”, Advances in Earth Science; Feb. 2005; vol. 20, No. 2; 6 pages.

Pan et al, “Research method of pore structure in tight reservoir”, Reservoir Evaluation and Development; 2014; 7 pages.

Yu et al, “Quantitative Research for Porosity Evolution in Low Permeability Deep Gas Reservoir of Rift-Subsidence Basin”, China Academic Journal Electronic Publishing House; Jun. 2010; vol. 21, No. 3; 9 pages.

Office Action for Chinese Patent Application No. 201410287262.0 dated Dec. 21, 2015 with translation; 7 pages.

Search report for Chinese Patent Application No. 201410287262.0 dated Dec. 21, 2015; 4 pages.

First Office Action and search report dated Jul. 21, 2016 for counterpart Canadian patent application No. 2,895,497.

* cited by examiner

CHARACTERIZATION METHOD FOR A RESERVOIR MICRO PORE STRUCTURE AND A SYSTEM THEREOF

CROSS-REFERENCE TO RELATED APPLICATIONS

This patent application claims the benefit of priority under 35 U.S.C. §119 from Chinese Patent Application No. 201410287262.0, filed Jun. 24, 2014. The disclosure of this application is incorporated herein by reference in its entirety.

TECHNICAL FIELD

The present application relates to the field of characterization of oil and gas reservoir, and in particular relates to a characterization method for a reservoir micro pore structure and a system thereof.

BACKGROUND ART

In oil and gas production, the reservoir is a porous medium that stores oil and gas. Many macroscopic properties of the reservoir (such as porosity, permeability and capillary pressure) depend on its micro structures, as well as on the physical properties of solids that compose it and fluids in the spaces of its pores. Therefore, in order to enhance the oil recovery remarkably, the theoretical study and technical development thereof should not stay on the macro level, but the research should be directed into the interiors of the porous medium on the micro level.

The oil and gas reservoir micro pore structure refers to the geometrical shapes, sizes, distributions and the interconnecting relationships of the pores and throats of reservoir rocks, generally on the micrometer (micron) scale (less than 1 millimeter) or smaller. The oil and gas reservoir micro pore structure decides the reservoir features, preserving mechanism and production process of the oil and gas resources, in particular, as for a tight sandstone reservoir which mainly comprises nanoscale micro pore structures, the micro pore structure thereof is an important factor that decides the pore permeability features thereof. Therefore, how to accurately characterize a reservoir micro pore structure has become an important topic in the process of oil-gas exploration.

Currently, the conventionally employed characterization method for a reservoir micro pore structure is CT scanning technology. The CT scanning technology is a technique that performs an all-around and large-scale scanning and imaging of a rock sample using X-ray and then reconstructs the micro pore 3D structural features using values of the scanned images. The CT scanning technology is classified into nanoscale CT and micron scale CT, wherein, the micron scale CT can only characterize pore structures over micron scale, of which the maximum resolution ratio is 0.7 micron; the nanoscale CT has a resolution ratio higher than that of the micron scale CT, but the maximum resolution ratio thereof during measuring process is also only 50 nm.

In oil and gas development, it is found that there are large amount of micro pore structures which are smaller than 50 nm in the unconventional reservoirs such as tight sandstone and shale etc. Since the maximum resolution ratio of the CT scanning technology is 50 nm, therefore it is hard to satisfy the requirements for the characterization of such micro pore structures by using conventional CT scanning technologies, and this has to some extent restricted the process of oil and gas exploration and development of the unconventional reservoir such as tight sandstone and shale etc. Therefore, there is an urgent need for a characterization method for a reservoir micro pore structure for characterizing a reservoir micro pore structure smaller than 50 nm.

SUMMARY

The present application provides a characterization method for a reservoir micro pore structure and a system thereof for characterizing a reservoir micro pore structure smaller than 50 nm.

The present application provides a characterization method for a reservoir micro pore structure, the method comprising the following steps:

fabricating a reservoir sheet;

fabricating a reservoir sheet electrode using the reservoir sheet;

depositing a crystal substance into pores of the reservoir sheet of the reservoir sheet electrode by using electrochemical deposition;

obtaining the crystal substance by removing a rock portion of the reservoir sheet in which the crystal substance is deposited;

scanning a morphology of the obtained crystal substance.

In another exemplary embodiment of an antenna assembly, the step of fabricating a reservoir sheet comprises:

oil washing a reservoir sample;

fabricating the oil washed reservoir sample into a reservoir sheet having a thickness of 100 nm-1 mm.

In another exemplary embodiment of an antenna assembly, the step of fabricating the reservoir sheet electrode comprises:

providing a conductive layer on part of a rock surface of the reservoir sheet;

cutting the reservoir sheet provided with the conductive layer;

electrically connecting the conductive layer of the cut reservoir sheet to a deposit electrode to obtain a primary reservoir sheet electrode;

performing insulating treatment to surfaces other than the rock surface of the primary reservoir sheet electrode to obtain the reservoir sheet electrode.

In another exemplary embodiment of an antenna assembly, the conductive layer has a thickness of 10 nm-30 nm, and is made by using one of platinum, gold, iridium, graphite and silver, or alloy materials comprising several ones of platinum, gold, iridium, graphite and silver.

In another exemplary embodiment of an antenna assembly, the cut reservoir sheet has a length and a width of 0.2 cm-0.6 cm.

In another exemplary embodiment of an antenna assembly, the conductive layer of the cut reservoir sheet is electrically connected to the deposit electrode using silver adhesive.

In another exemplary embodiment of an antenna assembly, the insulating treatment covers the surfaces other than the rock surface of the primary reservoir sheet electrode using epoxy resin.

In another exemplary embodiment of an antenna assembly, the deposit electrode is made by using one of platinum electrode, conductive glass electrode, gold electrode, iridium electrode, lead electrode, silver electrode and graphite electrode.

In another exemplary embodiment of an antenna assembly, the step of depositing the crystal substance comprises:

selecting as electrolyte one of chloroplatinic acid solution, gold chloride acid solution and silver nitrate solution with a concentration of 0.001 mol/L-0.1 mol/L;

immersing the reservoir sheet electrode into the electrolyte as a working electrode, controlling a deposition potential as −0.5 volts-−3 volts and controlling a deposit time as 10 min-10 hours.

In another exemplary embodiment of an antenna assembly, the step of obtaining the crystal substance comprises:

separating the reservoir sheet in which the crystal substance is deposited from the reservoir sheet electrode;

selecting as dissolving solution one of hydrofluoric acid, hydrochloric acid, nitric acid and phosphoric acid with a concentration of 0.001 mol/L-10 mol/L, or a mixed liquid of several ones of hydrofluoric acid, hydrochloric acid, nitric acid and phosphoric acid with a concentration of 0.001 mol/L-10 mol/L;

immersing the reservoir sheet in which the crystal substance is deposited into the dissolving solution and obtaining the crystal substance after the rock portion of the reservoir sheet in which the crystal substance is deposited is dissolved.

The present application also provides a system for characterizing the micro pore structure of reservoir based on the above mentioned characterization method, comprises:

a sheet fabricating apparatus for fabricating a reservoir sheet;

an electrode packaging apparatus for fabricating a reservoir sheet electrode using the reservoir sheet;

an electrochemical depositing apparatus for depositing crystal substance into pores of the reservoir sheet of the reservoir sheet electrode using electrochemical deposition;

an obtaining apparatus for obtaining the crystal substance by removing a rock portion of the reservoir sheet in which the crystal substance is deposited;

an analyzing and detecting apparatus for scanning a morphology of the obtained crystal substance.

In another exemplary embodiment of an antenna assembly, the sheet fabricating apparatus comprises a washing mechanism for oil washing a reservoir sample and a cutting and grinding mechanism for fabricating the oil washed reservoir sample into a reservoir sheet having a thickness of 100 nm-1 mm.

In another exemplary embodiment of an antenna assembly, the washing mechanism comprises a liquid container, a high-pressure pump, a core holder and a waste liquid receiver, which are sequentially connected with each other; the liquid container is used for accommodating and receiving an organic solvent; the high-pressure pump is used for applying pressure to the organic solvent; the core holder is used for accommodating the reservoir sample; the waste liquid receiver is used for receiving waste liquid exhausted from the core holder; and the cutting and grinding mechanism comprises a core cutter having a cutting disk and a core polishing disk having a mesh number of 100 to 2000.

In another exemplary embodiment of an antenna assembly, the electrode packaging apparatus comprises a conductive layer setting mechanism for providing a conductive layer on part of a rock surface of the reservoir sheet, a cutting mechanism for cutting the reservoir sheet provided with the conductive layer, a connecting mechanism for electrically connecting the conductive layer of the cut reservoir sheet to a deposit electrode to obtain a primary reservoir sheet, and an insulating mechanism for performing insulating treatment to surfaces other than the rock surface of the primary reservoir sheet electrode to obtain the reservoir sheet electrode.

In another exemplary embodiment of an antenna assembly, the conductive layer setting mechanism comprises a vacuum coating machine; the cutting mechanism comprises a blade; the connecting mechanism comprises silver adhesive; and the insulating mechanism comprises epoxy resin.

In another exemplary embodiment of an antenna assembly, the electrochemical depositing apparatus comprises a power supply, an electrode connected to the power supply, a controller that can control deposit voltage and deposit time, and a solution vessel that accommodates electrolyte; the electrode can stretch into the electrolyte; the electrode comprises a working electrode, a counter electrode and a reference electrode; the working electrode is the reservoir sheet electrode; the counter electrode is made by using one of platinum electrode, conductive glass electrode, gold electrode, iridium electrode, lead electrode, silver electrode and graphite electrode; the reference electrode is made by using one of mercury/mercuric sulfate electrode, mercury/mercuric oxide electrode, silver/silver chloride electrode, calomel electrode and hydrogen electrode.

In another exemplary embodiment of an antenna assembly, the obtaining apparatus comprises a separating mechanism for separating the reservoir sheet in which the crystal substance is deposited from the reservoir sheet electrode, a dissolving tank that accommodates a dissolving solution, and a washing tank that accommodates a cleaning solution.

In another exemplary embodiment of an antenna assembly, the analyzing and detecting apparatus comprises a field emission scanning electron microscope and/or an environmental scanning electron microscope.

Making use of the characteristic that metal or semiconductor can be deposited in pores smaller than 10 nm by using electrochemical deposition, the present application fabricates working electrodes using reservoir sheets, deposits metal ions in the reservoir micro pores and perform nano crystallization, and thus the finally obtained crystal substance can characterize the reservoir micro pore structure. The crystal substance can overcome the defect of the prior art that the CT scanning technology cannot characterize micro pore structures smaller than 50 nm, therefore the characterization resolution ratio is improved, which is advantageous for the study of the micro pore structure in the unconventional reservoir such as shale and tight sandstone and so on.

BRIEF DESCRIPTION OF THE DRAWINGS

In order to explain more clearly the embodiments in the present application or the technical solutions in the prior art, the following will briefly introduce the figures needed in the description of the embodiments or the prior art. Obviously, figures in the following description are only some embodiments of the present application, and for a person skilled in the art, other figures may also be obtained based on these figures without paying creative efforts.

DETAILED DESCRIPTION

For better understandings of those skilled in the art about the technical solutions in the present application, the following will provide explicit and complete descriptions of the technical solutions in the present application in combination with the figures of the embodiments of the present application. Obviously, the embodiments described hereinafter are only some of the embodiments of the present application rather than the entirety of the embodiments of the present application. Based on the embodiments of the present application, all other embodiments obtained by ordinary skilled persons in the field without paying creative efforts should pertain to the extent of protection of the present application.

Figure 1:
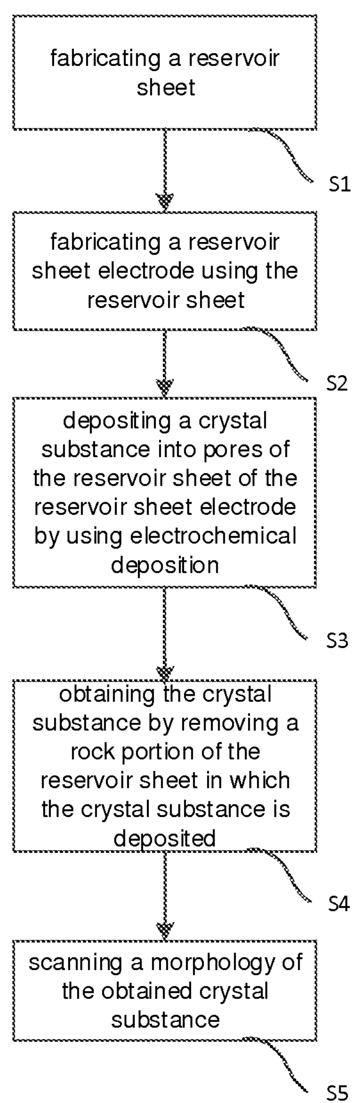
FIG. 1 is a flowchart illustrating a characterization method for a reservoir micro pore structure of the present application.

FIG. 1 is a characterization method for a reservoir micro pore structure provided by the embodiments of the present application. The characterization method for a reservoir micro pore structure of the present application comprises the following steps:

Step S1: Fabricating a Reservoir Sheet;

The fabricating of a reservoir sheet requires reservoir samples, which may be shale, sandstone, mudstone, volcanic and carbonate rocks, and may also be samples of core blocks, rock debris blocks or outcrop blocks. The collected reservoir samples usually have in their inner pores some impurities such as petroleum, and need to be washed. After washing out the impurities such as petroleum in the inner pores of the reservoir samples, the reservoir samples are cut and grinded to obtain the reservoir sheets, and the thickness of the reservoir sheet may be controlled between 100 nm-1 mm.

Step S2: Fabricating a Reservoir Sheet Electrode Using the Reservoir Sheet.

In this step, the required reservoir sheet electrode requires, in electrochemical deposition, the control of the metal ions to deposit in the inner micro pores of the reservoir sheet, thus it should be ensured that, in electrochemical deposition, the metal ions enter and deposit into the pores through a rock surface of the reservoir sheet, and the metal ions should not be deposited at any other parts of the reservoir sheet electrode. Further, insulating treatment needs to be performed to the reservoir sheet electrode except for the rock surface of the reservoir sheet thereof.

Thus, the process of fabricating the reservoir sheet electrode may be: providing a conductive layer on part of the rock surface of the reservoir sheet, the conductive layer covering and closely connecting to a part of the rock surface. The needed reservoir sheet electrode may have a length and a width of 0.2 cm-0.6 cm, so that the reservoir sheet provided with the conductive layer needs to be cut. Then, the conductive layer is electrical connected to a deposit electrode, and insulating treatment is perform to the surfaces other than the rock surface which is provided with no conductive layer, as such, it is ensured that the surface exposed in an electrolyte is just the rock surface.

Through the above manufacturing method, the metal ions in the electrolyte can enter into the micro pores of the reservoir sheet through the rock surface, and then contact the surfaces of a deposit electrode. As the deposition proceeds, the metal ions deposit in the pores of the reservoir sheet.

The deposit electrode may apply one of platinum electrode, gold electrode, conductive glass electrode, iridium electrode, lead electrode, silver electrode and graphite electrode.

The conductive layer may apply one of platinum, gold, iridium, graphite and silver, or alloy materials comprising several ones of platinum, gold, iridium, graphite and silver, which can have a thickness being controlled between 10 nm-30 nm. The process of providing the conductive layer may be placing a reservoir sheet in vacuum, and sputtering, onto part of a rock surface of the reservoir sheet, a conductive layer having a thickness between 10 nm-30 nm by using an ion sputtering method. The insulating treatment may be performed by applying methods such as spraying and cladding with insulating substances, for example, cladding the surfaces other than the rock surface which is provided with no conductive layer in the reservoir sheet electrode with epoxy resin, so as to achieve an insulating effect.

Step S3: Depositing a Crystal Substance into Pores of the Reservoir Sheet of the Reservoir Sheet Electrode Using Electrochemical Deposition.

Electrochemical deposition refers to the process that metal, alloy or metallic compound are deposited on the surface of the electrode in aqueous solutions, non-aqueous solutions or molten salts of their compounds, under the influence of an electrical field, and the process is usually accompanied with losing or gaining of electrons. In this step, the reservoir sheet electrode obtained in step S2 is immersed into the electrolyte by using the characteristic of electrochemical deposition, and metal ions in the electrolyte are deposited into the micro pores of the reservoir sheet by using a two electrode system or a three electrode system and a method of potentiostatic deposition.

In the electrochemical deposition, a deposition potential may be controlled between −0.5 volt-−3 volt, and the deposit time may be controlled between 10 min-10 hours, thereby a better deposition effect can be guaranteed. Correspondingly, a concentration of the electrolyte may be between 0.001 mol/L-0.1 mol/L, and the electrolyte may apply metal ions solutions, such as one of chloroplatinic acid solution, gold chloride acid solution and silver nitrate solution.

Step S4: Obtaining the Crystal Substance by Removing a Rock Portion of the Reservoir Sheet in which the Crystal Substance is Deposited.

In the above step S3, after the metal ions are deposited in the micro pores of the reservoir sheet, the morphology of the crystal substance produced by the deposition will adapt to the micro pore structure, thus, the scanning of the morphology of the crystal substance is able to characterize the micro pore structure of the stored reservoir sheet. The crystal substance needs to be obtained before scanning the crystal substance.

To obtain the crystal substance, first of all, the reservoir sheet in which the crystal substance is deposited needs to be taken down from the reservoir sheet electrode, and then the rock portion of the reservoir sheet in which the crystal substance is deposited is removed. The dissolving method can be is made by using as a method of the removal. When the dissolving method is made by using, the selected dissolving solution can have a concentration between 0.001 mol/L-10 mol/L, and the corresponding dissolving solution may be one of hydrofluoric acid, hydrochloric acid, nitric acid and phosphoric acid, and may also be a mixed solution of arbitrary several ones of the hydrofluoric acid, hydrochloric acid, nitric acid and phosphoric acid.

Step S5: Scanning the Morphology of the Obtained Crystal Substance.

After obtaining the crystal substance, the morphology of the obtained crystal substance can be scanned by using a scanning electron microscope. The scanning electron microscope comprises field emission scanning electron microscope and environmental scanning electron microscope, both of which can be is made by using in this step. A result of the scanning is the micro pore structure of the reservoir sheet.

Making use of the "cathodic deposition" of the electrochemical deposition and the characteristic thereof that metal ions can be deposited in pores smaller than 10 nm, the above embodiment provided in the present application fabricates working electrodes using the reservoir sheets, and performs nano crystallization by depositing metal ions in the reservoir micro pores, thereby the finally obtained crystal substance can characterize the reservoir micro pore structure. The crystal substance can overcome the defect in the prior art that the CT scanning technology cannot characterize micro pore structures smaller than 50 nm, therefore the characterization resolution ratio is improved, which is advantageous for the study of the micro pore structure in the unconventional reservoir such as shale and tight sandstone and so on. Preferably, pore structures are characterized using the present method on at least the micrometer (micron) scale (less than 1 millimeter), more preferably on the nanometer scale (i.e., pore sizes of less than 1 micrometer), and even more preferably pore sizes of less than 100 nanometers are characterized. The crystal substance obtained by using the characterization method provided in the present application has a 3D structure, therefore can intuitively scan the reservoir micro pore structure.

Figure 2:
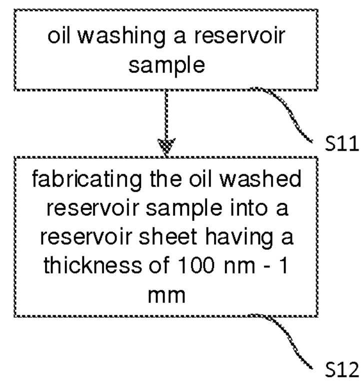
FIG. 2 is a flowchart illustrating the substeps of fabricating a rock sheet in a characterization method for a reservoir micro pore structure of the present application.

As shown in FIG. 2, in one embodiment of the present application, the step S1 comprises the following substeps:

Step S11: Oil Washing a Reservoir Sample.

In this embodiment, core sandstone blocks are selected as the reservoir sample. The purpose of performing oil washing to the core sandstone blocks is to wash out the substances such as petroleum in the inner pores of the core sandstone block, making the inner pores of the core sandstone blocks contain no filler, so as to be prepared for the subsequent electrochemical deposition.

Step S12: Fabricating the Oil Washed Reservoir Sample into a Reservoir Sheet Having a Thickness of Between 100 nm-1 mm.

At this time, firstly, the above oil washed core sandstone block is cut into primary core sandstone sheets, then the surfaces of the primary core sandstone sheets are grinded to be smooth, and the primary core sandstone sheets are polished to be sheets with a thickness of 100 microns, thereby obtaining the core sandstone sheets.

The core sandstone sheets may have a thickness between 100 nm-1 mm, and this embodiment selects the thickness of the core sandstone sheet as 100 microns.

Figure 3:
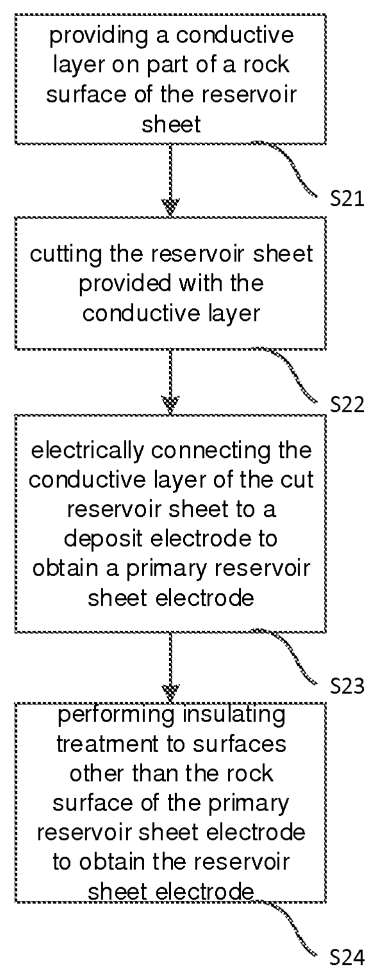
FIG. 3 is a flowchart illustrating the substeps of fabricating a reservoir sheet electrode in a characterization method for a reservoir micro pore structure of the present application.

As shown in FIG. 3, in another embodiment of the present application, the step S2 comprises the following substeps:

Step S21: Providing a Conductive Layer on a Rock Surface of the Reservoir Sheet Portion.

In order to ensure that metal ions in the electrolyte can enter into the micro pores of the reservoir sheet through the rock surface of the reservoir sheet and can contact the surface of a deposit electrode, there is a need to provide a conductive layer on part of the surface of the reservoir sheet to make it conductive, and thereby attract the metal ions into the interior of the micro pores of the reservoir sheet.

In this step, the providing of the conductive layer is realized in this embodiment in such a manner: placing a reservoir sheet in vacuum and sputtering a layer of platinum with a thickness of 20 nm onto its surface by using an ion sputtering method, thereby forming the conductive layer. At this time, the surfaces of the reservoir sheet comprise a rock surface and a conductive layer surface.

The conductive layer may apply one of platinum, gold, iridium, graphite and silver, or alloy materials comprising several ones of platinum, gold, iridium, graphite and silver, and may have a thickness being controlled between 10 nm-30 nm.

Step S22: Cutting the Reservoir Sheet Provided with the Conductive Layer;

In this step, a surface of the reservoir sheet provided with the conductive layer is required to be closely attached to the surface of the deposit electrode, therefore the surface area of the reservoir sheet should be controlled as not being larger than that of the deposit electrode. Thus, in this embodiment, the length and width of the core sandstone sheet covered with the platinum conductive layer are both cut as 0.4 cm.

The length and width of the core sandstone sheet covered with the platinum conductive layer are not limited to the mentioned 0.4 cm, and may be any length within the range of 0.2 cm-0.6 cm.

Step S23: Electric Connecting the Conductive Layer of the Cut Reservoir Sheet to a Deposit Electrode to Obtain a Primary Reservoir Sheet Electrode.

In order to ensure that the conductive layer can absorb metal ions, there is a need to electrically connect the conductive layer to the deposit electrode, so that while performing electrochemical deposition, the conductive layer can absorb and deposit the metal ions. The primary reservoir sheet electrode is obtained after the conductive layer of the cut reservoir sheet is electrically connected to the deposit electrode. At this time, the rock surface of the reservoir sheet in the step S21 is the rock surface of the primary reservoir sheet electrode.

In this step, the conductive layer of the cut reservoir sheet is closely attached to a surface of a platinum electrode via silver adhesive. The platinum electrode is the deposit electrode.

The method of electrical connection is not limited to the above mentioned method of adhering via silver adhesive, but may also use conductive adhesive and silver paste etc.

The deposit electrode is also not limited to applying the above platinum electrode, but may apply one of platinum electrode, gold electrode, conductive glass electrode, iridium electrode, lead electrode, silver electrode and graphite electrode.

Step S24: Performing Insulating Treatment to Surfaces Other than the Rock Surface of the Primary Reservoir Sheet Electrode to Obtain the Reservoir Sheet Electrode.

In order that the electrochemical deposition reaction only happens after entering the rock surface of the primary reservoir sheet electrode, there is a need to conduct insulating treatment to the surfaces other than the rock surface of the primary reservoir sheet electrode.

At this time, the insulating effect is achieved by using epoxy resin to clad the surface of the platinum electrode that has not been covered by the core sandstone sheet, and thereby the reservoir sheet electrode is obtained.

Figure 4:
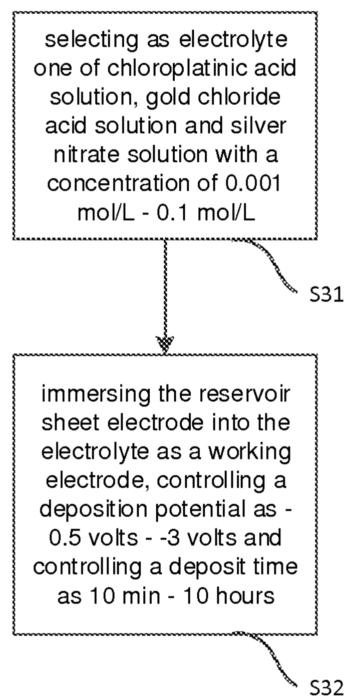
FIG. 4 is a flowchart illustrating the substeps of depositing crystal substance in a characterization method for a reservoir micro pore structure of the present application.

As shown in FIG. 4, in a feasible embodiment of the present application, the step S3 comprises the following substeps:

Step S31: Selecting as Electrolyte One of Chloroplatinic Acid Solution, Gold Chloride Acid Solution and Silver Nitrate Solution, all Having a Concentration of 0.001 mol/L-0.1 mol/L.

In the electrochemical deposition, the electrolyte for performing the electrochemical deposition needs to be selected in advance. In the present embodiment, the chloroplatinic acid solution with a concentration of 0.01 mol/L is selected as the electrolyte.

Step S32: Immersing the Reservoir Sheet Electrode into the Electrolyte as a Working Electrode, Controlling a Deposition Potential as −0.5 volts-−3 volts and Controlling a Deposit Time as 10 min-10 hours.

At this time, the reservoir sheet electrode is immersed into the chloroplatinic acid solution as working electrode, the two electrode system of electrochemical deposition as well as the method of potentiostatic deposition are is made by using, and the deposition potential is controlled as −1 volts while the deposit time is 2 hours. Upon reaching of the deposit time, the crystal substance will deposit in the pores of the core sandstone sheet of the reservoir sheet electrode.

In the electrochemical deposition, this embodiment is not limited to the above two electrode system and a three electrode system may also be applicable. Correspondingly, the deposition potential can be between −0.5 volts-−3 volts, and the deposit time can be between 10 min-10 hours.

Figure 5:
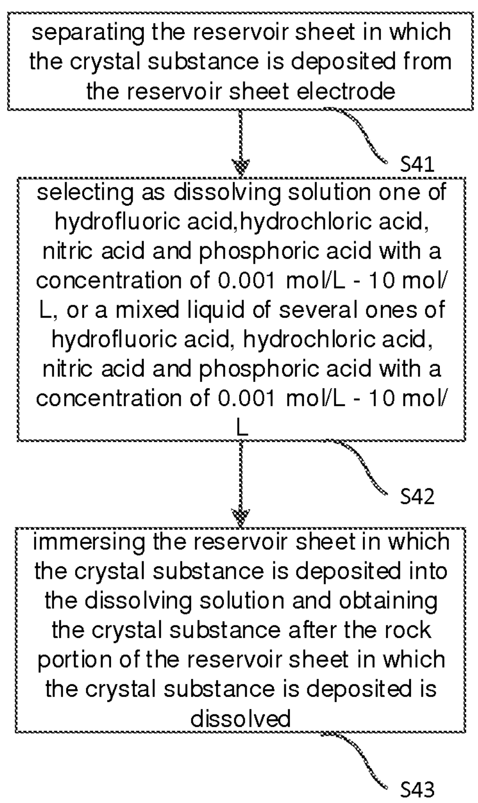
FIG. 5 is a flowchart illustrating the substeps of obtaining the crystal substance in a characterization method for a reservoir micro pore structure of the present application.

As shown in FIG. 5, in a specific embodiment of the present application, the step S4 comprises the following substeps:

Step S41: Separating the Reservoir Sheet in which the Crystal Substance is Deposited from the Reservoir Sheet Electrode;

In order to facilitate the removal of the rock portion of the reservoir sheet using a dissolving method in the following steps, there is a need to take down the reservoir sheet in which the crystal substance is deposited from the reservoir sheet electrode, and obtains the core sandstone sheet in which the crystal substance platinum is deposited.

Step S42: Selecting as Dissolving Solution One of Hydrofluoric Acid, Hydrochloric Acid, Nitric Acid and Phosphoric Acid with a Concentration of 0.001 mol/L-10 mol/L, or a Mixed Liquid of Several Ones of Hydrofluoric Acid, Hydrochloric Acid, Nitric Acid and Phosphoric Acid with a Concentration of 0.001 mol/L-10 mol/L;

In order to remove the rock portion of the reservoir sheet in which the crystal substance is deposited to obtain the crystal substance, this embodiment applies the dissolving method to remove the rock portion. The dissolving solution may have a concentration of between 0.001 mol/L-10 mol/L, and the corresponding dissolving solution may be one of hydrofluoric acid, hydrochloric acid, nitric acid and phosphoric acid, and may also be a mixed solution of arbitrary several ones of hydrofluoric acid, hydrochloric acid, nitric acid and phosphoric acid.

At this time, the hydrofluoric acid solution with a concentration of 0.01 mol/L is selected as the dissolving solution.

Step S43: Immersing the Reservoir Sheet in which the Crystal Substance is Deposited into the Dissolving Solution and Obtaining the Crystal Substance after the Rock Portion of the Reservoir Sheet in which the Crystal Substance is Deposited is Dissolved.

The reservoir sheet in which crystal substance is deposited is totally immersed into the hydrofluoric acid solution, and the dissolving time is controlled between 1 hour and 5 hours. After the rock portion of the core sandstone sheet in which the crystal substance platinum is deposited has completely been dissolved, the crystal substance is obtained, and the morphology of the crystal substance is the micro pore structure of the interior of the core sandstone sheet.

Figure 6:
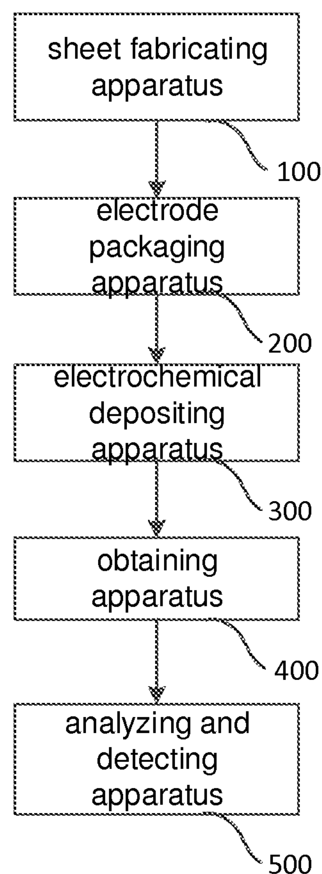
FIG. 6 is a schematic diagram of a characterization system for a reservoir micro pore structure of the present application.

With reference to FIG. 6, an embodiment of the present application provides a characterization system for a reservoir micro pore structure based on the characterization method provided in the above embodiment, comprising: a sheet fabricating apparatus 100 for fabricating a reservoir sheet; an electrode packaging apparatus 200 for fabricating a reservoir sheet electrode using the reservoir sheet; an electrochemical depositing apparatus 300 for depositing crystal substance in the inner pores of the reservoir sheet of the reservoir sheet electrode using electrochemical deposition; an obtaining apparatus 400 for removing the rock portion of the reservoir sheet in which the crystal substance is deposited; and an analyzing and detecting apparatus 500 for scanning the morphology of the obtained crystal substance.

When using the characterization system provided in this embodiment, first of all, the sheet fabricating apparatus 100 is used to fabricate a reservoir sample into a reservoir sheet; and the reservoir sheet is fabricated into a reservoir sheet electrode using the electrode packaging apparatus 200; then the electrochemical deposition apparatus 300 is used to deposit crystal substance in the inner pores of the reservoir sheet of the reservoir sheet electrode by electrochemical deposition; after that the crystal substance is obtained by using the obtaining apparatus 400 to remove the rock portion of the reservoir sheet in which the crystal substance is deposited; at last, the analyzing and detecting apparatus 500 is used to scan the morphology of the obtained crystal substance, thereby the reservoir micro pore structure is characterized.

It is clear from the above description that the characterization system proposed in this embodiment makes uses of the characteristic that metal or semiconductor can be deposited in the pores smaller than 10 nm by using electrochemical deposition, fabricates the working electrodes using reservoir sheets, deposits metal ions in the reservoir micro pores and performs nano crystallization, thereby the finally obtained crystal substance can characterize the reservoir micro pore structure. The crystal substance can overcome the defect of the prior art that the CT scanning technology cannot characterize the micro pore structure smaller than 50 nm, therefore the characterization resolution ratio can be improved, which is advantageous for the study of the micro pore structure in the unconventional reservoir such as shale and tight sandstone etc.

The sheet fabricating apparatus 100 comprises a washing mechanism for oil washing a reservoir sample and a cutting and grinding mechanism for fabricating the oil washed reservoir sample into a reservoir sheet having a thickness between 100 nm-1 mm.

Specifically, the washing mechanism oil washes the reservoir sample to wash out the substances such as petroleum in the inner pores of the reservoir sample, making the inner pores of the reservoir sample have no fillers, so as to be prepared for the subsequent electrochemical deposition. The washing mechanism comprises a liquid container, a high-pressure pump, a core holder and a waste liquid receiver, which are sequentially connected with each other; the liquid container is used for accommodating and receiving an organic solvent The organic solvent may comprises benzene and cyclohexane etc. The liquid container is mainly composed of one or more connected round cartridges or square cartridges that have a liquid inlet and a liquid outlet. The liquid inlet can input the organic solvent into the liquid container. The liquid outlet communicates the high-pressure pump via tubes. The high-pressure pump is used for apply pressure to the organic solvent, and thereby ensure that the reservoir sample can be washed sufficiently. The high-pressure pump also communicates with the core holder via tubes, so as to inject the pressurized organic solvent into the core holder. The core holder is used for accommodating the reservoir sample. The reservoir sample is washed by the organic solvent inside the core holder. The waste liquid receiver is connected to an end of the core holder via a tube. The waste liquid receiver is used for receiving the waste liquid exhausted from the core holder. Further, the waste liquid receiver may be a beaker or a plastic bucket.

The cutting and grinding mechanism may comprises a core cutter having a cutting disk and a core polishing disk having a mesh number of 100 to 2000. In practical operations, the cutting and grinding mechanism may first of all cut the reservoir sample into primary reservoir sample sheets, and then the core polishing disk can grind and polish the surface of primary reservoir sample sheets for ease of the subsequent providing of the conductive layer.

The electrode packaging apparatus 200 may comprise a conductive layer setting mechanism for providing a conductive layer on the rock surface of the reservoir sheet portion, a cutting mechanism for cutting the reservoir sheet of the provided conductive layer, a connecting mechanism for electric connecting the conductive layer of the cut reservoir sheet to the deposit electrode to obtain the primary reservoir sheet, and an insulating mechanism for performing insulating treatment to the surfaces other than the rock surface of the primary reservoir sheet electrode to obtain the reservoir sheet electrode.

Specifically, the conductive layer setting mechanism comprises a vacuum coating machine. The vacuum coating machine forms a metal layer having a certain thickness, i.e., the conductive layer, on the surface of the reservoir sheet by placing the reservoir sheet in vacuum and by using the method of ion sputtering. The cutting mechanism may comprise a blade. Now that the thickness of a reservoir sheet is small, manual cutting can be is made by using. The connecting mechanism may comprise silver adhesive. When applying the silver adhesive, the silver adhesive can be daubed manually on the conductive layer or the deposit electrode to adhere the two, and thereby the primary reservoir sheet electrode is formed. The insulating mechanism comprises epoxy resin. The epoxy resin is also manually daubed on the non-rock surfaces of the primary reservoir sheet electrode, thereby the reservoir sheet electrode is obtained.

The electrochemical deposition apparatus 300 may comprise: a power supply, an electrode connected with the power supply, a controller that can control deposit voltage and deposit time, and a solution vessel that accommodates electrolyte. The power supply comprises a voltage stabilized device having a stable output voltage or a current stabilized device having a stable output current such as electrochemical work station, potentiostat and galvanostat etc. The solution vessel is a container for containing electrolyte; the container is made of one of the following materials: metal, glass, plastic and organic glass. A concentration of the electrolyte may be between 0.001 mol/L-0.1 mol/L, and the electrolyte may apply metal ions solutions, such as one of chloroplatinic acid solution, gold chloride acid solution and silver nitrate solution.

The controller can control the deposit voltage and deposit time of the electrode, preferably, the controller can control the deposit potential as −0.5 volts-−3 volts, and control the deposit time as between 10 min-10 hours. The controller may be software, programs, and may also be PLC and industrial computer and so on. Specifically, the controller may comprise a testing and analyzing software comprised of one or more technical modules of constant current, constant voltage, constant power, constant resistance, cyclic voltammetry and alternating-current impedance.

The electrode can stretch into the electrolyte. The electrode may comprise a working electrode, a counter electrode and a reference electrode. The working electrode is the reservoir sheet electrode. The deposit electrode applies one of platinum electrode, conductive glass electrode, gold electrode, iridium electrode, lead electrode, silver electrode and graphite electrode. The reference electrode applies one of mercury/mercuric sulfate electrode, mercury/mercuric oxide electrode, silver/silver chloride electrode, calomel electrode and hydrogen electrode.

The obtaining apparatus 400 comprises a separating mechanism for separating the reservoir sheet in which the crystal substance is deposited from the reservoir sheet electrode, a dissolving tank that accommodates a dissolving solution and a washing tank that accommodates a cleaning solution. The dissolving solution may be one of hydrofluoric acid, hydrochloric acid, nitric acid and phosphoric acid with a concentration of 0.001 mol/L-10 mol/L, or a mixed liquid of several ones of hydrofluoric acid, hydrochloric acid, nitric acid and phosphoric acid with a concentration of 0.001 mol/L-10 mol/L. The cleaning solution may apply water. The dissolving tank and the washing tank can both apply beaker. The separating mechanism may comprise a heating plate or a liquid container, and correspondingly, the reservoir sheet in which the crystal substance is deposited is separated from the reservoir sheet electrode by heating or by immersing the reservoir sheet electrode in the liquid container containing the organic solvent such as acetone, benzene and cyclohexane etc.

The analyzing and detecting apparatus 500 comprises a field emission scanning electron microscope and/or an environmental scanning electron microscope. A result of the scanning is the micro pore structure of the reservoir sheet.

The above has shown and described the basic principle, main features and advantages of the present application. It shall be appreciated by those skilled in the art that, the present application is not limited by the above embodiments, the above embodiments and what described in the Description only illustrate the principles of the present application, without departing from the spirit of the present application, there are different variations and improvements for the present application, which should all be comprised in the protection scope of the present application. The protection scope of the present application is defined by the attached claims and the equivalents thereof.

The invention claimed is:

1. A characterization method for a reservoir micro pore structure, comprising the following steps:

fabricating a reservoir sheet;

fabricating a reservoir sheet electrode using the reservoir sheet;

depositing metal ions into pores of the reservoir sheet of the reservoir sheet electrode by using electrochemical deposition;

obtaining a metal deposition substance by removing a rock portion of the reservoir sheet in which the metal ions are deposited; and scanning a morphology of the metal deposition substance.

2. The characterization method for a reservoir micro pore structure of claim 1, wherein the step of fabricating a reservoir sheet comprises:

oil washing a reservoir sample; and fabricating the oil washed reservoir sample into a reservoir sheet having a thickness of between 100 nm and 1 mm.

3. The characterization method for a reservoir micro pore structure of claim 1, wherein the step of fabricating the reservoir sheet electrode comprises:

providing a conductive layer on part of a rock surface of the reservoir sheet;

cutting the reservoir sheet provided with the conductive layer;

electrically connecting the conductive layer of the cut reservoir sheet to a deposit electrode to obtain a primary reservoir sheet electrode; and performing insulating treatment to surfaces other than the rock surface of the primary reservoir sheet electrode to obtain the reservoir sheet electrode.

4. The characterization method for a reservoir micro pore structure of claim 3, wherein the conductive layer has a thickness of 10 nm-30 nm, and is made by using a material selected from the group consisting of platinum, gold, iridium, graphite and silver, and alloy materials thereof.

5. The characterization method for a reservoir micro pore structure of claim 3, wherein the cut reservoir sheet has a length and a width of between 0.2 cm and 0.6 cm.

6. The characterization method for a reservoir micro pore structure of claim 3, wherein, the conductive layer of the cut reservoir sheet is electrically connected to the deposit electrode using silver adhesive.

7. The characterization method for a reservoir micro pore structure of claim 3, wherein the insulating treatment covers the surfaces other than the rock surface of the primary reservoir sheet electrode using epoxy resin.

8. The characterization method for a reservoir micro pore structure of claim 3, wherein the deposit electrode is made by using an electrode selected from the group consisting of a platinum electrode, a conductive glass electrode, a gold electrode, an iridium electrode, a lead electrode, a silver electrode and a graphite electrode.

9. The characterization method for a reservoir micro pore structure of claim 1, wherein the step of depositing the metal deposition substance comprises:

selecting an electrolyte from the group consisting of a chloroplatinic acid solution, a gold chloride acid solution and a silver nitrate solution, wherein the electrolyte has a concentration of between 0.001 mol/L and 0.1 mol/L; and immersing the reservoir sheet electrode into the electrolyte as a working electrode, controlling a deposition potential of between −0.5 volts and −3 volts, and controlling a deposit time of between 10 minutes and 10 hours.

10. The characterization method for a reservoir micro pore structure of claim 1, wherein the step of obtaining the metal deposition substance comprises:

separating the reservoir sheet in which the metal deposition substance is deposited from the reservoir sheet electrode;

selecting a dissolving solution selected from the group consisting of hydrofluoric acid, hydrochloric acid, nitric acid, phosphoric acid, and a mixture of one or more of the foregoing acids, wherein the dissolving solution has a concentration of between 0.001 mol/L and 10 mol/L; and immersing the reservoir sheet in which the metal deposition substance is deposited into the dissolving solution and obtaining the metal deposition substance after the rock portion of the reservoir sheet in which the metal deposition substance is deposited is dissolved.

* * * * *